(12) United States Patent
Hanlon

(10) Patent No.: US 8,034,307 B2
(45) Date of Patent: Oct. 11, 2011

(54) FILTER FOR AUTOMATED SLIDE PREPARATION SYSTEM

(75) Inventor: David Hanlon, Derry, NH (US)

(73) Assignee: CYTYC Corporation, Marlborough, MA (US)

( * ) Notice: Subject to any disclaimer, the term of this patent is extended or adjusted under 35 U.S.C. 154(b) by 1362 days.

(21) Appl. No.: 11/550,688

(22) Filed: Oct. 18, 2006

(65) Prior Publication Data

US 2008/0095672 A1    Apr. 24, 2008

(51) Int. Cl.
*B01L 3/00*    (2006.01)
(52) U.S. Cl. ........ 422/558; 422/513; 422/534; 436/174; 436/177; 436/178
(58) Field of Classification Search .......... 422/100, 422/101, 102, 63, 68.1, 501, 509, 513, 527, 422/534, 547, 549, 558; 436/174, 177, 178
See application file for complete search history.

(56) References Cited

U.S. PATENT DOCUMENTS

| | | | |
|---|---|---|---|
| 3,799,342 A * | 3/1974 | Greenspan | 210/780 |
| 4,829,006 A * | 5/1989 | Smith et al. | 435/305.3 |
| 4,990,253 A * | 2/1991 | Vcelka | 210/359 |
| 5,143,627 A | 9/1992 | Lapidus et al. | |
| 5,240,606 A | 8/1993 | Lapidus et al. | |
| 5,282,978 A | 2/1994 | Polk, Jr. et al. | |
| 5,998,214 A * | 12/1999 | Guirguis | 436/165 |
| 6,221,655 B1 * | 4/2001 | Fung et al. | 435/288.1 |
| 6,562,299 B1 | 5/2003 | Ostgaard et al. | |
| 6,572,824 B1 | 6/2003 | Ostgaard et al. | |
| 2003/0175167 A1* | 9/2003 | Takanori et al. | 422/101 |
| 2003/0207455 A1 | 11/2003 | Ostgaard et al. | |
| 2003/0207456 A1 | 11/2003 | Ostgaard et al. | |

OTHER PUBLICATIONS

Piaton et al, "Conventional liquid-based techniques versus Cytyc Thinprep® processing of urinary samples: a qualitative approach," BMC Clinical Pathology, 5:9. Published online Oct. 6, 2005, BioMed Central Ltd.

* cited by examiner

*Primary Examiner* — Jill Warden
*Assistant Examiner* — Dwayne K Handy
(74) *Attorney, Agent, or Firm* — Vista IP Law Group LLP

(57) ABSTRACT

A vessel for collecting biological particulate matter suspended in fluid includes a body having first and second ends and a fluid passageway there between. A filter member is disposed at one of the first and second ends of the body, the filter member having a porosity that permits passage of fluid but retains at least a portion of the biological particular matter. The exterior surface of the body portion includes at least one agitation member. The agitation member may be formed, for instance, as a blade, fin, projection, helical ring, or other protuberance.

19 Claims, 4 Drawing Sheets

Figure 5:
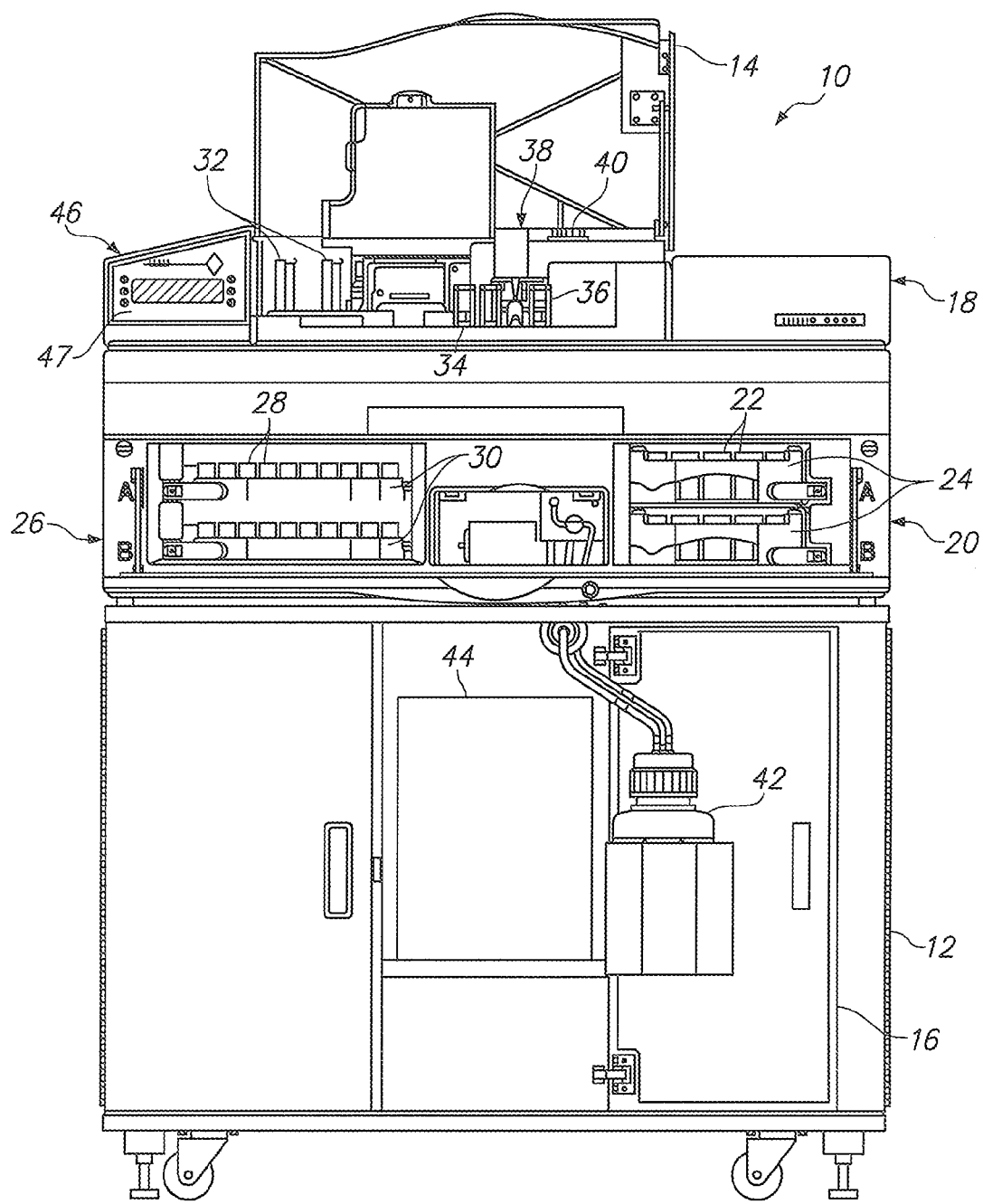

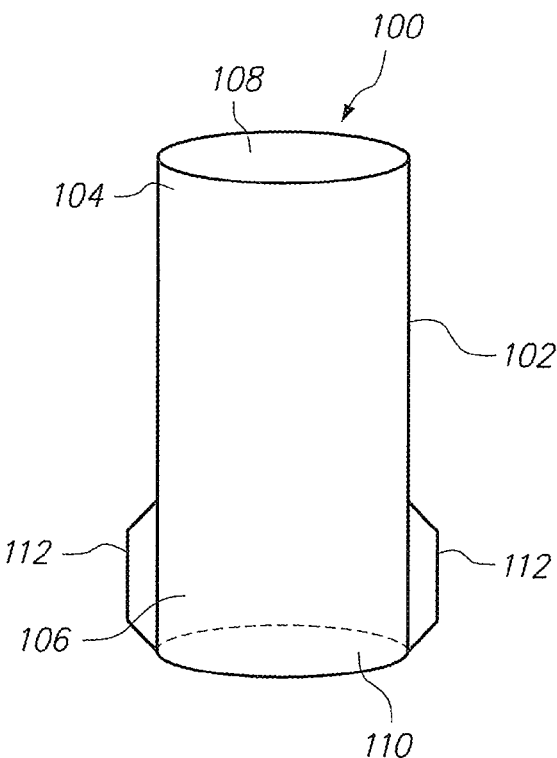
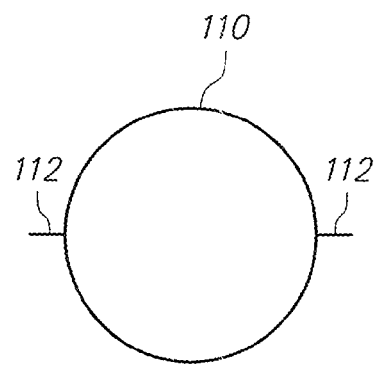
FIG. 1A  FIG. 1B
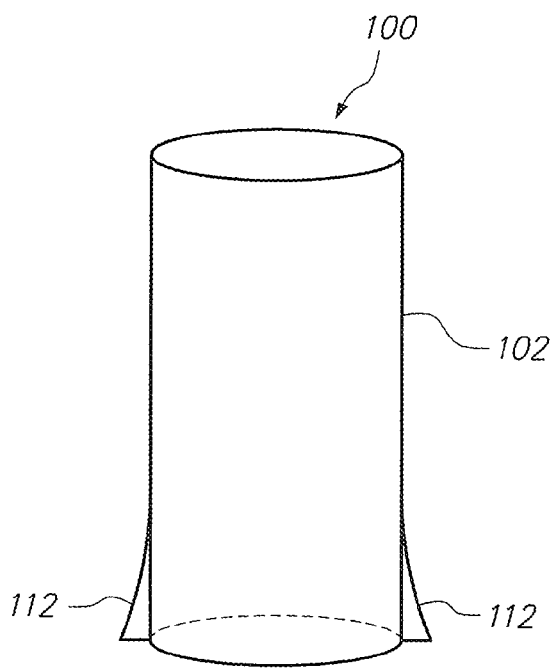
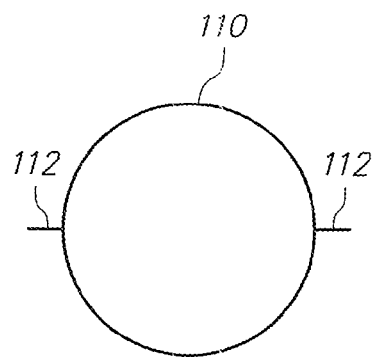
FIG. 2A  FIG. 2B

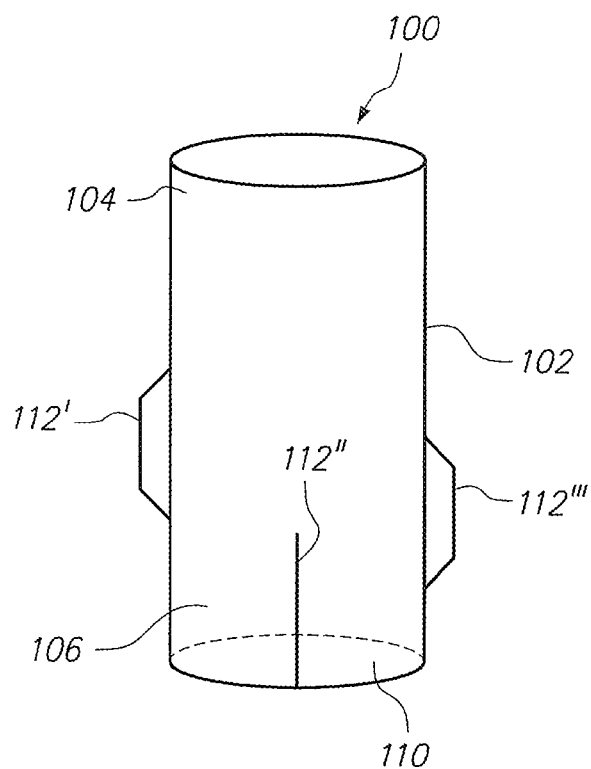
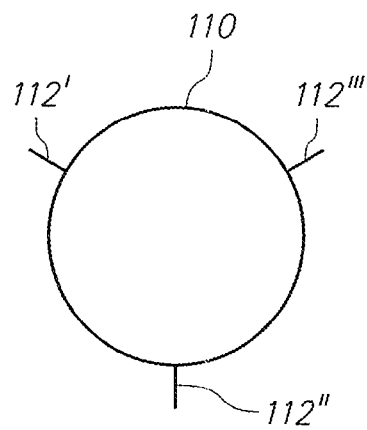
FIG. 3A
FIG. 3B
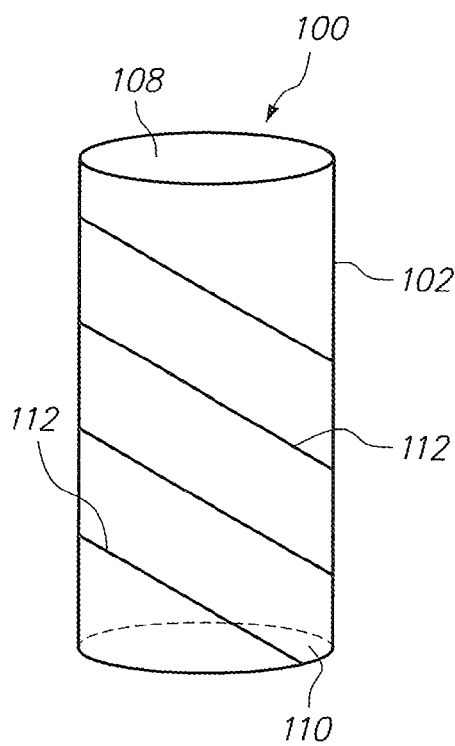
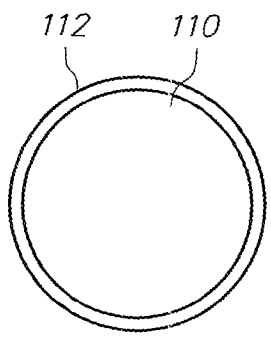
FIG. 4A
FIG. 4B

FILTER FOR AUTOMATED SLIDE PREPARATION SYSTEM

FIELD OF THE INVENTION

The present invention relates to a filter designed for use with automated slide preparation systems for analyzing biological materials.

BACKGROUND

Automated slide preparation systems for analyzing biological materials are known in the art. For example, U.S. Pat. Nos. 5,143,627, 5,282,978, and 6,562,299, and U.S. Patent Application Publication Nos. 2003-0207455 A1 and 2003-0207456 A1, all of which are incorporated herein by reference in their entirety, describe such automated systems. Some or all of these slide preparation systems employ a collection vessel having a filter that is introduced into the sample liquid and onto which a selected quantity of the dispersed sample of cells are collected. A pressure system connected with the collection vessel draws sample liquid into the vessel for collecting the cells on the filter surface.

In automated slide preparation systems, it is often desired that the biological sample, from which cells are obtained, be agitated prior to cell collection. Agitation of the sample causes cell clusters, bits of tissue, and mucous to break up and create a relatively homogenous sample of cellular material. Some automated slide preparation systems agitate the biological sample by immersing the vessel having the filter into the biological sample and rotating the vessel at high speeds. The high speed rotation causes the biological sample solution to rotate as well, which causes the necessary agitation and mixing of the solutions. However, the high speed rotation also causes small amounts of the mixture to aerosolize or splash out of the vial containing the biological sample, thereby increasing the chances of cross-contamination.

SUMMARY OF THE INVENTION

In one embodiment, a vessel for collecting biological particulate matter suspended in fluid includes a body having first and second ends and a fluid passageway there between. A filter member is disposed at one of the first and second ends of the body, the filter member having a porosity that permits passage of fluid but retains at least a portion of the biological particular matter. The exterior surface of the body portion includes at least one agitation member. The agitation member may be formed, for instance, as a helically wound ring, blade, fin, projection, or other protuberance.

The agitation member(s) may be oriented substantially parallel to the long axis of the body. Alternatively, the agitation member(s) may be arranged at an angle with respect to the long axis of the body. At least one agitation member is preferably located at or adjacent to the filter member. Multiple agitation members may be populated on the exterior surface of the body. The agitation members may be arranged symmetrically about the circumference of the body or they may be arranged in a non-symmetrical manner.

In one aspect of the invention, the at least one agitation member is porous or contains holes or apertures for increasing mixing turbulence. In addition, the at least one agitation member may be constructed from a material that dissolves in the fluid, thereby limiting use of the vessel to a single use. This prevents the same vessel from being used multiple times, thereby avoiding cross-contamination.

In another embodiment, a method of collecting a biological sample includes providing a vessel of the type disclosed above. The vessel is immersed into a container holding the biological sample in a liquid. At least a portion of the vessel is submerged below the surface of the liquid. The vessel is rotated so as to agitate the liquid. The now mixed liquid solution is then drawn through the filter member so as to collect the biological sample on the filter member.

In still another embodiment, a vessel for collecting biological particulate matter suspended in fluid includes a body having first and second ends and a fluid passageway there between. Filter means is disposed at one of the first and second ends of the body, the filter means having a porosity that permits passage of fluid but retains at least a portion of the biological particular matter. For example, the agitation means may include a porous membrane. The exterior surface of the body portion includes at least one agitation means.

BRIEF DESCRIPTION OF THE DRAWINGS

FIG. 1A depicts an embodiment of the filter vessel having two agitation members.

FIG. 1B is a top view of the embodiment shown in FIG. 1A.

FIG. 2A depicts an embodiment of the filter vessel having two tapered agitation members.

FIG. 2B is a top view of the embodiment shown in FIG. 2A.

FIG. 3A depicts an embodiment of the filter vessel having three agitation members disposed at different distances from the filter.

FIG. 3B is a top view of the embodiment shown in FIG. 3A.

FIG. 4A depicts an embodiment of the filter vessel having a helical raised ring agitation member.

FIG. 4B is a top view of the embodiment shown in FIG. 4A.

FIG. 5 is schematic front view of an automated specimen processing apparatus in accordance with one embodiment of the present invention.

FIG. 6 is a schematic perspective view of a sample collector during cell collection in accordance with one embodiment of the present invention.

DETAILED DESCRIPTION OF THE ILLUSTRATED EMBODIMENTS

FIG. 1A shows an embodiment of a vessel 100 for collecting biological particulate matter. As used herein, biological particulate matter may include cells, cellular organelles, cellular debris, tissue, or other cellular material that may be viewed using pathological imaging techniques known to those skilled in the art. The vessel 100 includes a body 102 that has first and second ends 104, 106 and a fluid passageway 108 there between. The fluid passageway 108 may be formed from a central lumen or the like that passes through the body 102. The body 102 may be formed from a biologically inert material such as a polymer or plastic material. The shape of the vessel 100 is typically a hollow cylinder having a circular cross-sectional shape, although vessels 100 having other cross-sectional geometries are contemplated to fall within the scope of the invention. For example, the vessel 100 may have a cross-sectional shape of an ellipse (or oval) or a polygon, such as a triangle, a square, a rectangle, a pentagon, a hexagon, a heptagon, or an octagon, and the like. The vessel 100 may also take the shape of a vial or the like that is commonly used in other biological and chemical applications.

Still referring to FIG. 1, a filter member 110 is located at one end (e.g., 106) of the body 102 and covers the opening that provides access to the fluid passageway 108. The filter member 110 may take the form of a permeable membrane or the like. For example, a membrane having pores or a porosity on the order of several microns may be used (~5 µm). Generally, the filter member 110 is a membrane-type filter having a porosity to block sample cells that are to be collected and to pass smaller cells and other particles, as well as the cell-suspending liquid, relatively freely. In one illustrated preferred embodiment, the filter member 110 is a polycarbonate membrane having a porosity of 5 micrometers, as marketed by Nuclepore Corporation, in Pleasanton, Calif., U.S.A.

The filter member 110 may be bonded to the end 106 of the body 102. Additional details regarding the filter member 110 and its construction may be seen in U.S. Pat. No. 5,240,606 which is incorporated by reference as if set forth fully herein. The other end 104 of the body 102 is configured to attach to a pressure system. During operation, the vessel 100 is connected to the pressure system and is immersed in a container containing a biological sample suspended in a liquid. The pressure system, which may be a negative pressure or vacuum system, causes the liquid to be drawn into the vessel 100 via the filter member 110. Cells and particles of a certain size (e.g., those having an effective diameter >5 µm) are collected on the filter member 110 whereas the liquid and smaller particles pass through the filter member 110 and into the vessel 100 (inside passageway 108).

Prior to the aspiration of liquid into the vessel 100, it is preferable to stir or mix the biological sample so that any cell clusters, non-diagnostic debris, mucous, or blood is broken. Prior art methods spun a vessel in the biological sample at high speeds. However, as stated above, this resulted in aerosolized liquid, which may result in cross-contamination of samples.

The vessel 100 disclosed herein confers the advantage of spinning the filter vessel at lower speeds, so that the chance of spilling or aerosolizing the liquid out of the container holding the liquid is minimized. While the vessel 100 described herein can be spun at lower speed, good dispersion and mixing of the fluid suspension is still achieved. The vessel 100 accomplishes this by one or more agitation members 112 disposed on an exterior surface of the body 102 of the vessel 100.

During operation, when the vessel 100 spins in the liquid, the one or more agitation members 112 causes the liquid to mix with a greater force than if the members(s) 112 is/are absent. The agitation members 112 also aid in dispersing any clusters or masses of biological material contained in the liquid. Therefore, the vessel 100 having the agitation member(s) 112 can stir the liquid more gently and at lower speeds, while adequately mixing the sample. Likewise, because the vessel 100 is spun at a low rotational speed, there is little or no chance that liquid will aerosolize or spill. Cross-contamination can thus be avoided.

As seen in FIGS. 1A and 2A, the agitation members 112 may be disposed adjacent to the filter member 110 on one side 106 of the body 102. In other embodiments, such as that disclosed in FIG. 3A, the agitation members 112 are disposed along various points on the exterior surface of the body 102. The agitation members 112 may be formed from any number of shapes and geometries. For example, the agitation members 112 may include a projection, blade, fin (e.g., FIGS. 2A and 2B), or protuberance. The body 102 may have a single agitation member 112, for instance, as shown by the spiral, ring, or threaded configuration of FIGS. 4A and 4B, or the body 102 may contain multiple (more than two) agitation members 112.

FIGS. 1A, 1B, 2A, 2B, 3A, and 3B illustrate agitation members 112 that are arranged symmetrically about the exterior surface of the body 102. For example, in FIGS. 1A and 1B, there are two agitation members 112 located at opposite sides of the body. In an alternatively embodiment, the agitation members 112 may be arranged in a non-symmetrical manner. As seen in FIGS. 1A, 1B, 2A, 2B, 3A, and 3B, the agitation members 112 are arranged substantially parallel to the long axis of the body 102 (the axis passing through the fluid passageway 108 from the first end 104 to the second end 106). However, in an alternative embodiment, the agitation members 112 are arranged at an angle with respect to the long axis of the body 102.

The agitation members 112 may be disposed equidistant from the filter member 110 (e.g., FIGS. 1A and 2A). In an alternative aspect, the agitation members 112 are staggered and positioned at different distances from the filter member 110. FIG. 3A shows an embodiment in which there are three agitation members 112 located about the exterior surface of the body 102. Agitation member 112' is positioned furthest away from the filter member 110, and agitation member 112" is located closest to the filter member 110, while agitation member 112''' is positioned in between.

FIGS. 4A and 4B illustrate an alternate embodiment wherein a single agitation member 112 wraps around the exterior surface of the body 102. The agitation member 112 may take the form of a spiral, ring, or thread. FIG. 4A illustrates a helically oriented, raised ring (e.g., a cork screw, or a thread) structure 112, much like what is found on a drill bit, or on the neck of a bottle configured to receive a threaded cap. The raised ring structure 112 may circumscribe all or a portion of the exterior surface of the body 102. The raised ring structure 112 may be integrally formed with the body 102. Alternatively, the raised ring structure 112 may be formed separately and bonded or otherwise affixed to the exterior surface of the body 102. The raised ring structure 112 may be secured using a weld, heat-bond, or an adhesive.

Referring to the embodiments of FIGS. 1A, 1B, 2A, 2B, 3A, 3B, 4A, and 4B, in one aspect of the invention, the one or more agitation members 112 are formed as a solid structure. In an alternative aspect, however, the one or more agitation members 112 have holes or are made of a porous material. An agitation member 112 having holes and/or a porous structure creates additional turbulence that causes better mixing.

Still referring to the embodiments of FIGS. 1A, 1B, 2A, 2B, 3A, 3B, 4A, and 4B in another aspect of the invention, the at least one agitation member 112 is constructed from a material that is soluble in the fluid carrying the biological material. For instance, the agitation member 112 may be soluble in water and/or alcohol, or a preservative solution. The dissolvable agitation member 112 provides several benefits. For example, after the vessel 100 is used a certain number of times (e.g., once), the agitation member 112 dissolves away. In this regard, a user of the vessel 100 would not be able to reuse the vessel 100 for filtering multiple samples and, therefore, the chances of cross-contamination between the samples is greatly reduced. The agitation member 112 may be constructed such that the entirety of the agitation member 112 dissolves during use. Alternatively, it is possible that only a portion of the agitation member 112 dissolves after use. Material that can be used for the manufacture of a soluble structure 112 includes, but is not limited to, polyvinyl alcohol (PVA), acrylic resin, water-soluble melanin, alcohol-soluble melanin, and the like, or a combination thereof.

As explained above, in certain embodiments, an adhesive or other bonding agent may be used to bond the agitation member(s) 112 to the body 102. Consequently, the adhesive or bonding agent may be soluble within the carrying fluid (e.g., water and/or alcohol soluble or preservative). In these embodiments, after the vessel 100 is used, the adhesive dissolves in the liquid containing the biological sample and the agitation member(s) 112 break away from the body 102 of the vessel 100, again reducing the chances of cross-contamination by preventing the use of a single vessel 100 for multiple, repeated samples. Water and/or alcohol soluble adhesives include, but are not limited to, Aquabond 55™, Aquabond 65™, Aquabond 85™ (Aquabond Technologies, Camarillo, Calif.), combinations with PVA, combinations with polyvinylpyrrolidone (PVP), and the like, or a combination thereof.

During operation, a vessel 100 of the type disclosed herein is provided. The vessel 100 may be stored in an automated sample preparation device (not shown) that is used to automatically generate slides containing the biological sample for subsequent imaging and analysis. The vessel 100 is immersed into the fluid or liquid containing the biological sample of interest. The vessel 100 is lowered to a depth such at least a portion of the body 102 of the vessel 100 is submerged below the surface of the fluid. The filter member 110 is submerged under the fluid as well.

Typically, the vessel 100 is connected to a pressure system that draws sample liquid into the vessel 100 for collecting the cells on the filter surface. The pressure system may be a negative pressure system that provides pulsed, negative pressure on the backside of the body 102. In this regard, fluid can be pulled through the filter member 110 as explained below.

Once the vessel 100 is immersed in the fluid, the vessel 100 is rotated within the container containing the fluid and biological sample. The vessel 100 is rotated through the use of an automated drive mechanism (not shown). For example, the vessel 100 may be rotated by the use of a mechanically coupled motor or servo. U.S. Pat. No. 6,572,824 discloses a sample preparation apparatus that may be used in connection herewith. The '824 patent is incorporated by reference as if set forth fully herein. The vessel 100 is rotated or spun at a rotational speed that causes cell clusters, blood, or mucous present in the biological sample to break apart or disperse. Importantly, however, the rotational speed of the vessel 100 is low enough such that the liquid containing the sample does not aerosolize or spill out of the container.

As seen in FIG. 5, the system 10 (depicted with an upper cover 14 and front door 16 in open positions) includes a specimen preparing apparatus 18 or transferrer, functionally of the type disclosed in the aforementioned patents subject to improvements discussed further hereinbelow. Namely, the specimen preparing apparatus 18 includes subassemblies for automatically dispersing, collecting, and transferring a monolayer of cells to an analytical element, such as a microscope slide.

Figure 6:
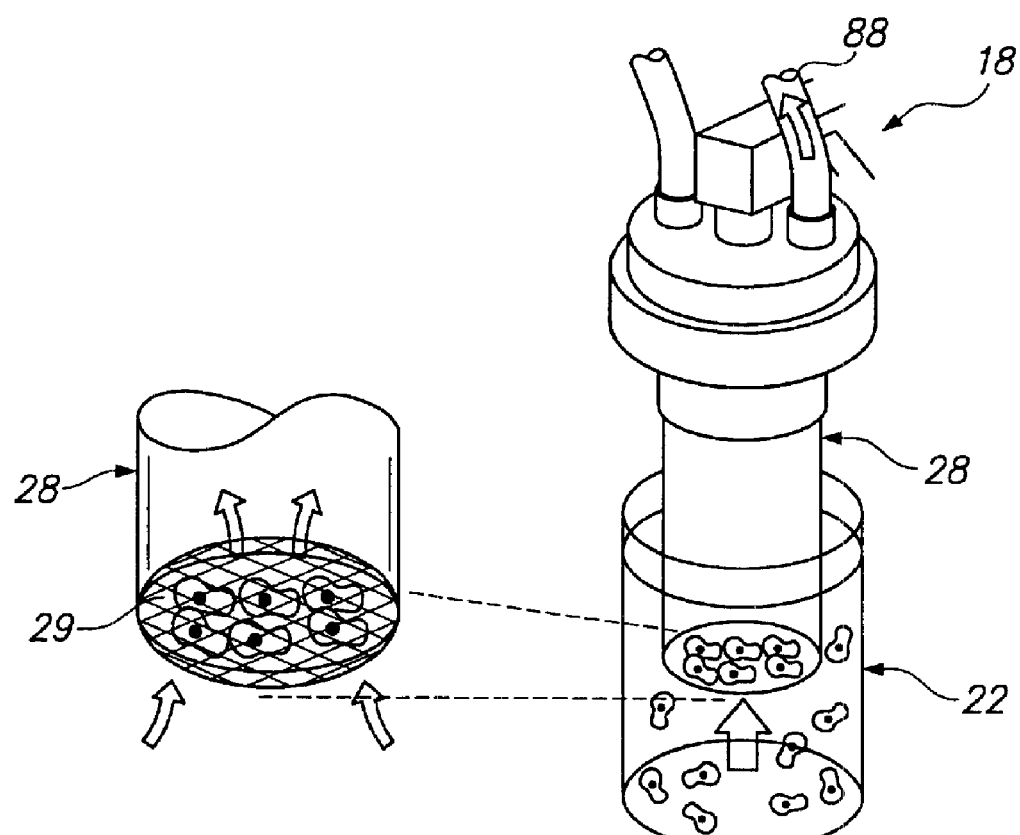

The sample vial transfer assembly 52 removes the cap 56 from the sample vial 22a so that the specimen preparing apparatus 18 can cycle. A sample collector 28 is taken automatically from the collector tray 30 at the second loading station 26 and inserted into the specimen preparing apparatus 18. Thereafter, the membrane 29 of the collector 28 is inserted into the specimen vial 22a to a predetermined depth as shown in FIG. 6 and, in one embodiment, the collector 28 is rotated to disperse the cells in the preservative fluid. A vacuum system 88 applies a controlled pressure and vacuum cycle to the collector 28 so that cells are collected in a monolayer against the membrane 29. The cells are subsequently transferred to the zone within the frosted annulus 70 on the slide 62.

The vessel 100 may be rotated in a single direction to disperse the biological material. For example, the vessel 100 may be rotated in either the clockwise or counter-clockwise directions. Alternatively, the vessel 100 may alternate between rotation in the clockwise direction and rotation in the counter-clockwise direction. In this regard, rotation may resemble certain wash cycles found in washing machines for clothing.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

What is claimed is:

1. A system for processing biological particulate matter suspended in fluid, the system comprising:
    a container holding a fluid having biological particulate therein;
    a filter body having first and second ends and a fluid passageway there between;
    a filter member disposed at the second end of the body, the filter member having a porosity that permits passage of the fluid therethrough, while retaining at least a portion of the biological particular matter on an exterior surface thereof;
    at least one agitation member disposed on an exterior surface of the body; and
    a mechanism for gripping the first end of the filter body and immersing the second end of the filter body into the fluid container so that the filter is in the fluid, wherein the mechanism is further configured to rotate the filter body relative to the container after the second end is immersed in the fluid, such that the at least one agitation member contacts the fluid when the filter body is rotated.

2. The system of claim 1, wherein the at least one agitation member is arranged substantially parallel to a long axis of the filter body.

3. The system of claim 1, wherein the at least one agitation member is arranged at an angle with respect to the long axis of the filter body.

4. The system of claim 1, wherein the at least one agitation member is arranged adjacent to the filter member.

5. The system of claim 1, wherein a plurality of agitation members are disposed on the exterior surface of the filter body.

6. The system of claim 5, wherein the plurality of agitation members are symmetrically arranged about the exterior surface of the filter body.

7. The system of claim 5, wherein the plurality of agitation members are non-symmetrically arranged about the exterior surface of the filter body.

8. The system of claim 1, wherein the at least one agitation member comprises a fin.

9. The system of claim 1, wherein the at least one agitation member comprises a helically-shaped ring about the exterior surface of the filter body.

10. The system of claim 1, wherein the at least one agitation member is porous.

11. The system of claim 1, wherein the at least one agitation member is formed from a material that dissolves in the fluid.

12. The system of claim 1, wherein the at least one agitation member is formed from a material that is soluble in water.

13. The system of claim 1, wherein the at least one agitation member is formed from a material that is soluble in alcohol.

14. The system of claim 1, wherein the at least one agitation member is attached to the exterior surface of the filter body by an adhesive.

15. The system of claim 14, wherein the adhesive is formed from a material that is soluble in the fluid.

16. A method of collecting a biological sample, the method comprising:

providing a filter body having first and second ends and a fluid passageway there between, a filter member disposed at one of the first and second ends of the filter body, the filter member having a porosity that permits passage of fluid therethrough while retaining biological particular matter in the fluid on an exterior surface of the filter member, and at least one agitation member disposed on an exterior surface of the filter body;

immersing the filter body into a container holding a liquid having the biological sample suspended therein, such that at least a portion of the filter body including the filter member and the at least one agitation member is below the surface of the liquid;

rotating the filter body relative to the container so that the at least one agitation member agitates the liquid; and passing the liquid through the filter member so as to collect the biological sample on the exterior surface of the filter member.

17. A method of collecting a biological sample, comprising:

providing a filter body having first and second ends and a fluid passageway there between, a filter member disposed at one of the first and second ends of the filter body, the filter member having a porosity that permits passage of fluid therethrough while retaining biological particular matter in the fluid on an exterior surface of the filter member, and at least one agitation member disposed on an exterior surface of the filter body;

immersing the filter body into a container holding a biological sample suspended in a liquid such that at least a portion of the filter body including the filter member and the at least one agitation member is below the surface of the liquid;

rotating the filter body relative to the container so that the at least one agitation member agitates the liquid; and passing the liquid through the filter member so as to collect the biological sample on the exterior surface of the filter member, wherein the at least one agitation member at least partially dissolves during the rotation step.

18. The method of claim 17, wherein during rotation of the filter body, the rotation rate of the filter body is maintained such that substantially no liquid is aerosolized.

19. The method of claim 16, wherein the filter body is first rotated in a first direction for a period of time, and rotated in a second direction for a period of time.

* * * * *